United States Patent
Cheng et al.

(10) Patent No.: US 11,998,312 B2
(45) Date of Patent: Jun. 4, 2024

(54) SYSTEMS AND METHODS FOR BREATHING DETECTION AND RATE ESTIMATION USING WIRELESS COMMUNICATION SIGNALS

(71) Applicant: NXP USA, INC., Austin, TX (US)

(72) Inventors: Xilin Cheng, Menlo Park, CA (US); Xiayu Zheng, San Jose, CA (US); Zhipei Chi, Sunnyvale, CA (US)

(73) Assignee: NXP USA, Inc., Austin, TX (US)

( * ) Notice: Subject to any disclaimer, the term of this patent is extended or adjusted under 35 U.S.C. 154(b) by 760 days.

(21) Appl. No.: 17/038,456

(22) Filed: Sep. 30, 2020

(65) Prior Publication Data

US 2022/0095950 A1 Mar. 31, 2022

(51) Int. Cl.
*A61B 5/08* (2006.01)
*A61B 5/00* (2006.01)
*G16H 50/30* (2018.01)
*H04W 24/08* (2009.01)

(52) U.S. Cl.
CPC .......... *A61B 5/0816* (2013.01); *A61B 5/0004* (2013.01); *A61B 5/7214* (2013.01); *A61B 5/7257* (2013.01); *G16H 50/30* (2018.01); *H04W 24/08* (2013.01)

(58) Field of Classification Search
None
See application file for complete search history.

(56) References Cited

U.S. PATENT DOCUMENTS

| | | | |
|---|---|---|---|
| 9,731,089 B2 | 8/2017 | Ahmad et al. | |
| 9,731,978 B2 | 8/2017 | Zhu et al. | |
| 10,495,725 B2 | 12/2019 | Zhang et al. | |
| 10,531,425 B2 | 1/2020 | Alonso | |
| 10,531,426 B2 | 1/2020 | Zheng et al. | |
| 10,694,491 B2 | 6/2020 | Zheng et al. | |
| 2019/0178980 A1* | 6/2019 | Zhang ............... | A61B 5/7267 |
| 2020/0068522 A1* | 2/2020 | Zheng ............... | H04B 17/336 |
| 2020/0178835 A1* | 6/2020 | Liu .................... | A61B 5/024 |
| 2020/0300972 A1* | 9/2020 | Wang ................ | A61B 5/1126 |

(Continued)

FOREIGN PATENT DOCUMENTS

CN 108553108 A 9/2018

OTHER PUBLICATIONS

Lee et al. "Design and implementation of monitoring system for breathing and heart rate pattern using WiFi signals," 2018 15th IEEE Annual Consumer Communications & Networking Conference (CCNC), Las Vegas, NV, USA, 2018, pp. 1-7. (Year: 2018).*

(Continued)

*Primary Examiner* — Meredith Weare

(57) ABSTRACT

Various embodiments relate to a method for estimating a breathing rate, including: receiving a plurality of channel state information (CSI) from a wireless device; selecting an initial reference CSI from the plurality of CSI; computing a perturbation index using the initial reference CSI and a portion of the plurality of CSI; determining an optimal reference CSI based upon the perturbation index; re-computing the perturbation index using the optimal reference CSI on a portion of the plurality of CSI subsequent to the optimal reference CSI; and determining a breathing rate from the perturbation index using a frequency analysis of the perturbation index.

20 Claims, 4 Drawing Sheets

(56) References Cited

U.S. PATENT DOCUMENTS

2021/0186369 A1* 6/2021 Wei ..................... A61B 5/7278

OTHER PUBLICATIONS

Ma et al. "WiFi Sensing with Channel State Information: A Survey." ACM Comput. Surv. 52, 3, Article 46 (Jun. 2019), 36 pages. (Year: 2019).*

Hao et al. "An Animal Respiration Monitoring System Based on Channel State Information of Wi-Fi Network." Published: Mar. 20, 2020. (Year: 2020).*

C. Chen, Y. Han, Y. Chen, F. Zhang, H. Q. Lai, B. Wang, and K. J. R. Liu, "TR-BREATH: Time-reversal breathing rate estimation and detection", IEEE Trans. Biomed. Eng., vol. 65, No. 3, pp. 489-501. (Mar. 2018).

* cited by examiner

SYSTEMS AND METHODS FOR BREATHING DETECTION AND RATE ESTIMATION USING WIRELESS COMMUNICATION SIGNALS

TECHNICAL FIELD

Various exemplary embodiments disclosed herein relate generally to systems and methods for breathing detection and rate estimation using wireless communication signals.

BACKGROUND

Monitoring respiration rate is important because it can help to detect and prevent abnormal respiratory rates that can lead to cardiac arrest, chronic obstructive pulmonary disease, and health problems. Today, most medical measurement and monitoring devices are either invasive or wired but people are hesitant to attach physiological sensors to their body. Because breathing detection and rate estimation is essential for human health monitoring, alternative methods for breathing detection and rate estimation would be beneficial.

SUMMARY

A summary of various exemplary embodiments is presented below. Some simplifications and omissions may be made in the following summary, which is intended to highlight and introduce some aspects of the various exemplary embodiments, but not to limit the scope of the invention. Detailed descriptions of an exemplary embodiment adequate to allow those of ordinary skill in the art to make and use the inventive concepts will follow in later sections.

Various embodiments relate to a method for estimating a breathing rate, including: receiving a plurality of channel state information (CSI) from a wireless device; selecting an initial reference CSI from the plurality of CSI; computing a perturbation index using the initial reference CSI and a portion of the plurality of CSI; determining an optimal reference CSI by finding the CSI associated with the maximum perturbance index value; re-computing the perturbation index using the optimal reference CSI on a portion of the plurality of CSI subsequent to the optimal reference CSI; and determining a breathing rate from the perturbation index using a frequency analysis of the perturbation index.

Various embodiments are described, wherein computing a perturbation index includes using channel nulling.

Various embodiments are described, wherein channel nulling includes: calculating a nulling matrix; and applying the nulling matrix to the plurality of CSI subsequent to the optimal reference CSI.

Various embodiments are described, wherein computing a perturbation index $F_{ii}$ includes computing:

$$\Gamma_n = 10 \log_{10} |\Sigma_{k,k+1 \in \Psi} \overline{\Delta h}_k^n \,^H \overline{\Delta h}_{k+1}^n| - 10 \log_{10} \Sigma_{k,k+1 \in \Psi} \|h_k^n\|^2,$$

where $\overline{\Delta h}_k^n$ is channel change information for CSIn, $h_k^n$ is the CSI for sample n, $\Psi$ is the set of all the available tones, and k is tone index.

Various embodiments are described, wherein determining a breathing rate includes: calculating the standard deviation of the perturbance index over a window set of values; and indicating a breathing detection failure when the standard deviation is below a predetermined threshold value.

Various embodiments are described, wherein the frequency analysis includes: performing a frequency transformation of the perturbance index over a window set of values; and determining the breathing rate as the frequency with the highest value.

Various embodiments are described, further including: calculating a peak-to-total power ratio using the frequency value with the highest value; and indicating a breathing detection failure when the peak-to-total power ratio is below a predetermined threshold value.

Various embodiments are described, further comprising sliding the window set of values and re-calculating the breathing rate.

Various embodiments are described, further including: determining a breathing rate detection failure; computing an average of the perturbation values of the window set of values; indicating motion when the average of the perturbation values is above a predetermined threshold; and indicating no motion when the average of the perturbation values is below a predetermined threshold.

Further various embodiments relate to a breathing rate estimation system, including: a receiver configured to receive a plurality of channel state information (CSI) from a wireless device; a memory; and a processor connected to the receiver and memory configured to: select an initial reference CSI from the plurality of CSI; compute a perturbation index using the initial reference CSI and a portion of the plurality of CSI; determine an optimal reference CSI by finding the CSI associated with the maximum perturbance index value; re-compute the perturbation index using the optimal reference CSI on a portion of the plurality of CSI subsequent to the optimal reference CSI; and determine a breathing rate from the perturbation index using a frequency analysis of the perturbation index.

Various embodiments are described, wherein computing a perturbation index includes using channel nulling.

Various embodiments are described, wherein channel nulling includes: calculating a nulling matrix; and applying the nulling matrix to the plurality of CSI subsequent to the optimal reference CSI.

Various embodiments are described, wherein computing a perturbation index $F_{ii}$ includes computing:

$$\Gamma_n = 10 \log_{10} |\Sigma_{k,k+1 \in \Psi} \overline{\Delta h}_k^n \,^H \overline{\Delta h}_{k+1}^n| - 10 \log_{10} \Sigma_{k,k+1 \in \Psi} \|h_k^n\|^2,$$

where $\overline{\Delta h}_k^n$ is channel change information for CSIn, $h_k^n$ is the CSI for sample n, $\Psi$ is the set of all the available tones, and k is tone index.

Various embodiments are described, wherein determining a breathing rate includes: calculating the standard deviation of the perturbance index over a window set of values; and indicating a breathing detection failure when the standard deviation is below a predetermined threshold value.

Various embodiments are described, wherein the frequency analysis includes: performing a frequency transformation of the perturbance index over a window set of values; and determining the breathing rate as the frequency with the highest value.

Various embodiments are described, wherein the processor is further configured to: calculate a peak-to-total power ratio using the frequency value with the highest value; and indicate a breathing detection failure when the peak-to-total power ratio is below a predetermined threshold value.

Various embodiments are described, wherein the processor is further configured to slide the window set of values and re-calculate the breathing rate.

Various embodiments are described, wherein the processor is further configured to: determine a breathing rate detection failure; compute an average of the perturbation values of the window set of values; indicate motion when the average of the perturbation values is above a predetermined threshold; and indicate no motion when the average of the perturbation values is below a predetermined threshold.

BRIEF DESCRIPTION OF THE DRAWINGS

In order to better understand various exemplary embodiments, reference is made to the accompanying drawings, wherein.

To facilitate understanding, identical reference numerals have been used to designate elements having substantially the same or similar structure and/or substantially the same or similar function.

DETAILED DESCRIPTION

The description and drawings illustrate the principles of the invention. It will thus be appreciated that those skilled in the art will be able to devise various arrangements that, although not explicitly described or shown herein, embody the principles of the invention and are included within its scope. Furthermore, all examples recited herein are principally intended expressly to be for pedagogical purposes to aid the reader in understanding the principles of the invention and the concepts contributed by the inventor(s) to furthering the art and are to be construed as being without limitation to such specifically recited examples and conditions. Additionally, the term, "or," as used herein, refers to a non-exclusive or (i.e., and/or), unless otherwise indicated (e.g., "or else" or "or in the alternative"). Also, the various embodiments described herein are not necessarily mutually exclusive, as some embodiments can be combined with one or more other embodiments to form new embodiments.

Breathing rate is one of the main human vital signs (others may include body temperature, blood pressure, and pulse). The normal breathing rate for an adult at rest is within the range from 12 to 20 breaths per minute. A breathing rate outside of the normal range may require further consideration and may be caused by illness, medical conditions, fatigue, and/or psychological conditions. Therefore, breathing detection and rate estimation is essential for human health monitoring. Current solutions of breathing detection and rate estimation include an under-mattress device used during sleeping, a chest band/strap on an individual's body used during daily activities, a seat cover sensor placed inside driver seat used during driving, etc. However, current solutions require direct contact with measurement devices and/or extra installation effort is required.

Figure 1:
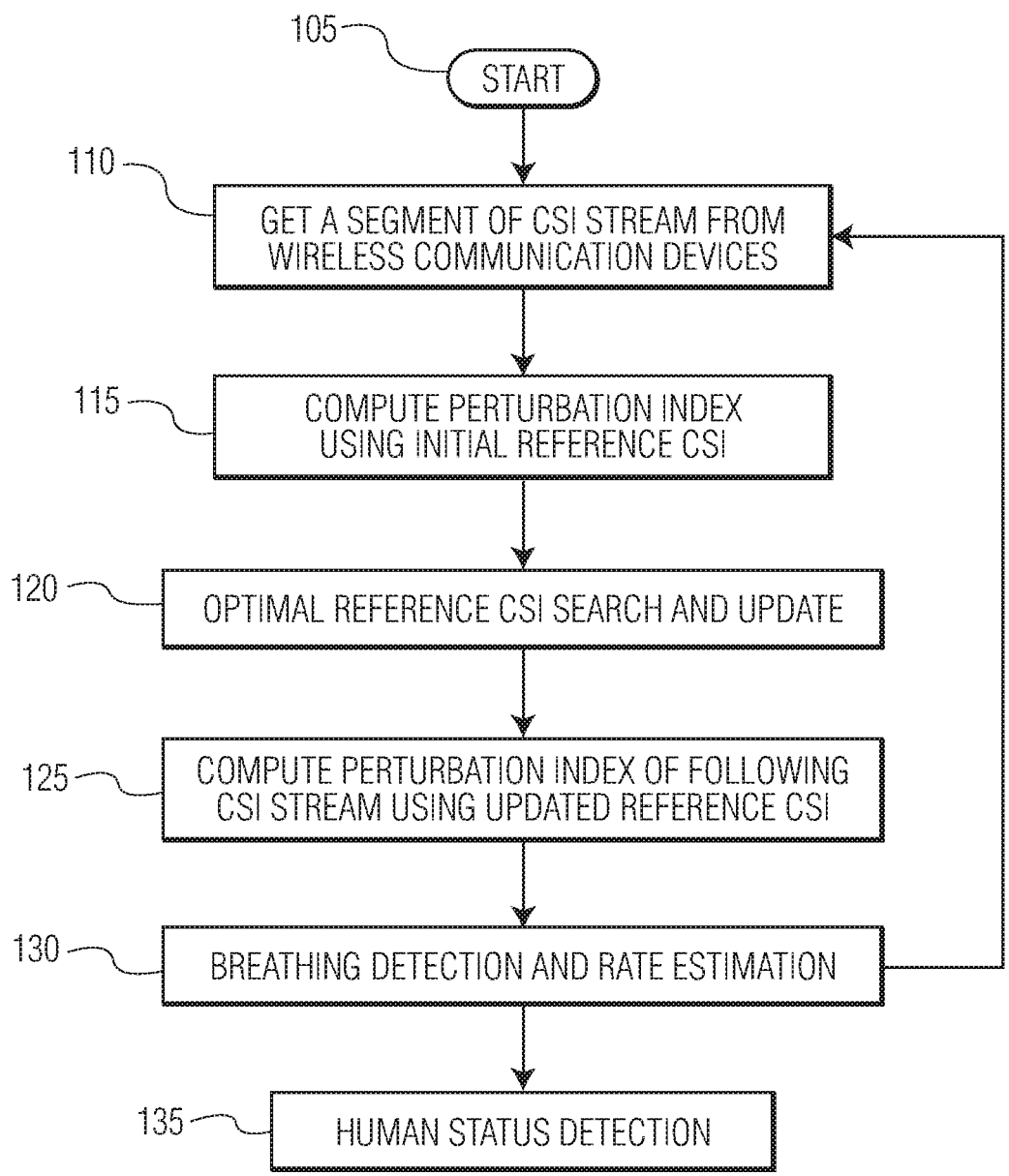
FIG. 1 illustrates a flow diagram illustrating the operation of the breathing detection and rate estimation system.

Embodiments of a breathing detection and rate estimation system using wireless communication signals is described herein. The system includes a first wireless communication device communicating with a second wireless communication device, and the second wireless communication device measuring channel state information (CSI) between the first and second wireless communication devices. FIG. 1 illustrates a flow diagram illustrating the operation of the breathing detection and rate estimation system. First, the system starts 105, and the CSI signal stream is segmented 110. Second, for a given CSI signal segment, an initial perturbation index signal is computed only for the beginning part of the CSI segment 115. The perturbation index signal indicates changes in the wireless environment. For example, an individual breath can cause changes to the wireless environment that can lead to a perturbation index signal that may be analyzed to detect breathing and the breathing rate. Channel nulling techniques may be utilized to extract wireless environment change, i.e., perturbation index signal caused by breathing. Third, based on the initial perturbation index signal, the system searches for an optimal reference CSI and the optimal reference CSI is updated 120. The process leads to determining the maximum inspiratory or expiratory point. Fourth, using the optimal reference CSI, the perturbation index signal is re-computed over the whole CSI segment after the reference CSI 125. Fifth, breathing detection and rate estimation is performed by applying a fast Fourier transform (FFT) on the perturbation index signal 130. Note, other frequency analysis techniques may be used as well. The FFT is able to extract and detect periodic signals such as a signal based upon periodic breathing. This may be done by identifying the frequency with the highest output power. Finally, the breathing detection and rate estimation system is further extended to a human status detection system 135. The system may be used to detect large movements of individuals in the field of the wireless signals. The proposed breathing detection and rate estimation system described herein is passive because the individual does not have to carry or touch any devices. As Wi-Fi devices are widely available, the breathing detection and rate estimation system built on top of these devices will have low cost and are almost installation free. It is noted that the various methods and techniques may be applied to wireless systems other than Wi-Fi as described herein.

Each of these steps will now be described in more detail. In a wireless communication system, a first wireless communication device (e.g., Wi-Fi client) communicates with a second wireless communication device (e.g., Wi-Fi access point (AP)). The second wireless communication device may continually output CSI signals with a millisecond granularity. Such Wi-Fi devices may include routers, access points, laptop and desktop computers, mobile phones, tablets, video streaming devices, smart watches, smart home devices, internet of things device, etc.

As previously discussed, breathing is a periodic motion and will periodically change the wireless channel between the Wi-Fi transmitter and receiver. The channel change may be reflected in the CSI signal measurement.

To start, the first packet in the segment of the CSI stream is set as the reference packet, i.e., $h_k^{ref}=h_k^0$, where k is tone index. The CSI of a later received packet n is $h_k^n=h_k^{ref}+\Delta h_k^n$, n>0, where $\Delta h_k^n$ represents the wireless channel change caused by breathing movement.

Next, the perturbation index is computed using the initial reference CSI. To extract channel change information $\Delta h_k^n$ caused by breathing movement, the reference CSI $h_k^{ref}$ has to be canceled. This may be achieved by constructing a nulling matrix $q_k$ based on the reference CSI such that $q_k^H h_k^{ref}=0$ and applying the nulling matrix to the latter CSIs as follows:

$$\overline{\Delta h}_k^n = q_k^H h_k^n = q_k^H (h_k^{ref}+\Delta h_k^n) = q_k^H \Delta h_k^n,$$

where $(*)^H$ is the conjugate transpose of the matrix $(*)$.

One way of constructing nulling matrix is using the Gram-Schmidt process method where:

$$q_k = q_{k,tmp}/\|q_{k,tmp}\| \text{ and}$$

where $$q_{k,tmp} = \left(I - \frac{h_k^{ref} h_k^{refH}}{\|h_k^{ref}\|^2}\right) u_0,$$

and $u_0$ comes from columns of a unitary matrix. There are also other ways of constructing the nulling matrix $q_k$ as long as $q_k^H h_k^{ref} = 0$, e.g., removing $u_0$ from previous equation and let $$q_k = I - \frac{h_k^{ref} h_k^{refH}}{\|h_k^{ref}\|^2}.$$

The perturbation index (in dB) is defined as the perturbation amount caused by breathing movement to the CSI:

$$\Gamma_n = 10 \log_{10} |\Sigma_{k,k \in \Psi} \overline{\Delta h}_k^n \overline{\Delta h}_{k+1}^n| - 10 \log_{10} \Sigma_{k,k+1 \in \Psi} \|h_k^n\|^2,$$

where $\Psi$ is the set of all the available tones. The more a current CSI deviates from the reference CSI, the larger the value of perturbation index is.

Figure 2A:
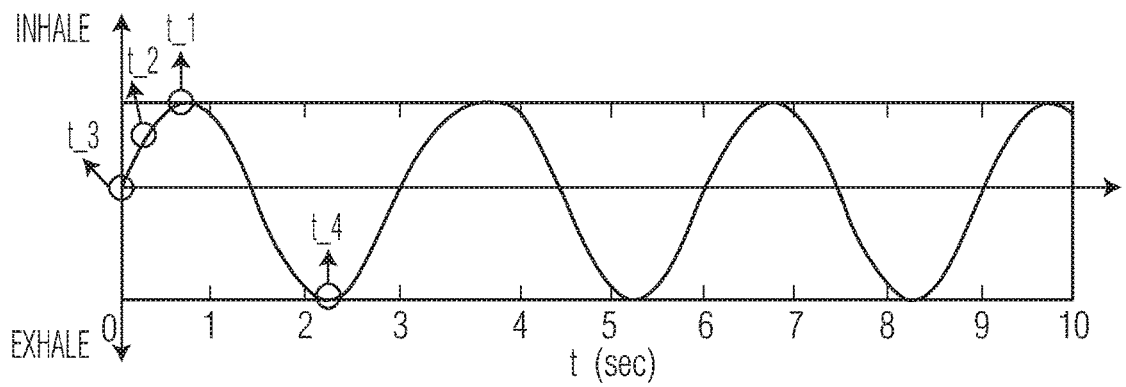
FIG. 2A illustrates a chest displacement curve during the periodic breathing of an individual.
Figure 2B:
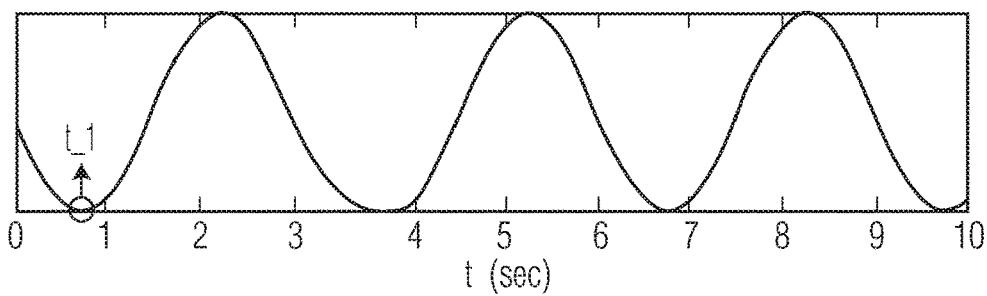
FIGS. 2B, 2C, and 2D are plots of the perturbation index using a CSI at t_1, t_3, and t_2 respectively.
Figure 2C:
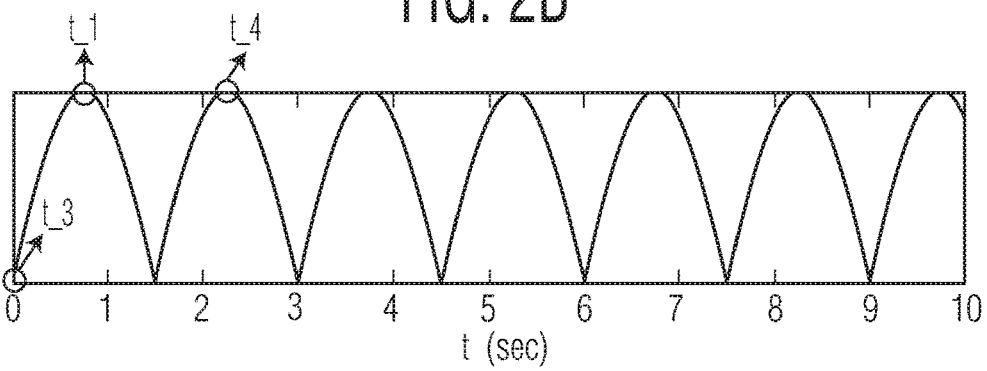
Figure 2D:
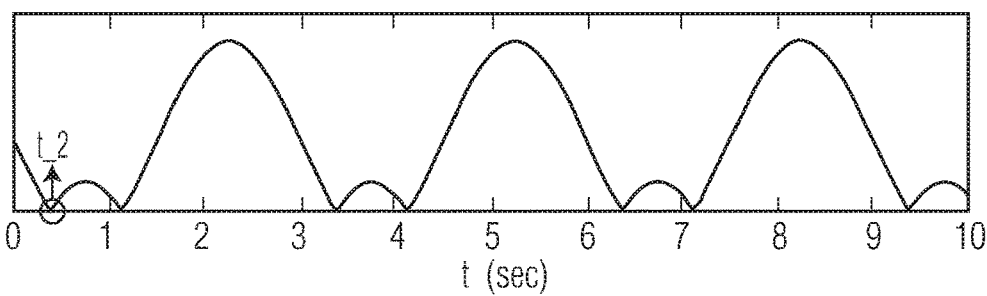

It will now be explained why the reference CSI is updated. FIG. 2A illustrates a chest displacement curve during the periodic breathing of an individual. The chest displacement curve has a period of $1/f_b$ with a breathing rate of $f_b$. FIGS. 2B, 2C, and 2D are plots of the perturbation index using a CSI at t_1, t_3, and t_2 respectively. As can be seen, the perturbation index changes when CSIs at the different times are used as the reference CSI. The maximum inspiratory point occurs at time t_1. The maximum expiratory point occurs at time t_4. The middle of maximum inspiratory/expiratory points occurs at time t_3. The displacement at time t_2 is some random displacement other than the maximum, minimum, and median displacement.

As illustrated in FIG. 2B, when the CSI at t_1 is selected as the reference point, the maximum perturbation index value occurs at t_4 as the chest at t_4 has largest displacement compared with t_1, i.e., the different in displacement is the largest.

As illustrated in FIG. 2C, when the CSI at time t_3 is selected as the reference point, the perturbation index reaches maximum at both t_1 and t_4, as chest at t_1 and t_4 has the same displacement compared with t_1. This causes main frequency component of perturbation index to be $2f_b$. Therefore, an inappropriate selection of the reference CSI could generate double breathing rate frequency component in perturbation index curve.

As illustrated in FIG. 2D, when the CSI at time t_2 is selected as the reference point, the perturbation index reaches maximum at t_4 with a local maximum resulting at t_1. This also may cause a frequency component of perturbation index to be found at $2f_b$ which could result in incorrect determination of the breathing frequency.

As a result, the reference CSI is updated to the CSI at the maximum inspiratory or expiratory point to avoid the incorrect determination of the breathing frequency.

A method for searching for the optimal reference CSI will now be described. With the found optimal reference CSI, the perturbation index is then recalculated using this new reference CSI.

Suppose every $T_p$ seconds, there is a CSI measurement. As mentioned before, the first received CSI $CSI_0$ is initially set as reference CSI, namely $CSI_{ref} = CSI_0$.

Next, in a first step, the reference CSI $CSI_{ref}$ is used to compute perturbation index $PI_n$ of subsequent CSIs $CSI_n$ where: $1 \leq n \leq \lceil \alpha/(f_b^{min} T_p) \rceil$; $f_b^{min}$ is the minimum breathing rate that the system is required to detect; $1/(f_b^{min} T_p)$ is maximum number of CSI measurements in a single period of breathing; and $\alpha$ is the coefficient to determine the CSI search window. It is noted that $\alpha$ has to be larger than ¾ to make sure the maximum inspiratory or expiratory point may be found.

In a second step, the index of the maximum value of the perturbation index $PI_n$ computed in the first step is found as:

$$\hat{n} = \underset{1 \leq n \leq \lceil \alpha/(f_b^{min} T_p) \rceil}{\arg\max} PI_n$$

Then, in a third step, $CSI_{\hat{n}}$ is used as optimal reference CSI, namely $CSI_{ref} = CSI_{\hat{n}}$.

With the updated reference CSI, the system may perform breathing detection and rate estimation. After updating the reference CSI $CSI_{ref} = CSI_{\hat{n}}$, the perturbation index $PI_n$ of subsequent $CSI_n$, where $\hat{n} < n$ may be re-computed.

The breathing rate is estimated over a PI sliding window containing $$\{PI(w) | PI(w) = PI_{\hat{n}+s+w}, w = 0, 1, \ldots N-1\},$$

where N is the window size and s>0 is the offset of window starting point.

In a first step the standard deviation of the PI values in the window is calculated as:

$$\sigma = STD(\{PI(w)\}).$$

If $\sigma < \sigma_{th}$, where $\sigma_{th}$ is a predetermined threshold, then indicate a failure to detect a breathing rate and output $f_b(\hat{n}+s) = 0$ and go to the fourth step, otherwise go to the next step.

In a second step, the peak frequency is searched for. First a frequency transformation is performed on the PI values as follows:

$$X(k) = FFT(\{PI(w)\}), k = 0, 1, \ldots, N-1.$$

While an FFT is method shown for performing the frequency transformation, other known methods may be used as well.

The peak frequency index is determined as:

$$k_{max} = \arg \min_{\lceil f_b^{min} T_p N \rceil \leq k \leq \lceil f_b^{max} T_p N \rceil} |X(k)|,$$

where $[f_b^{min}, f_b^{max}]$ is the range within which the breathing rate is detected.

Next, in a third step, a peak-to-total power ratio is calculated as follows:

$$\alpha = \frac{|X(k_{max})|^2}{\sum_{k \neq 0} |X(k)|^2}.$$

If $\alpha < \alpha_{th}$, where $\alpha_{th}$ is a predetermined threshold, then indicate a failure to detect a breathing rate and output $f_b(\hat{n}+s) = 0$, otherwise output the estimated breathing rate as:

$$f_b(\hat{n}+s) = \frac{k_{max}}{T_p N}.$$

In a fourth step the window is slide by calculating $s=s+\Delta s$ and then the method goes back to the first step.

The breathing rate estimation algorithm is able to track breathing rate change over time by using a sliding estimation window. The first step rules out the case where the windowed PI waveform has little variation. The second step finds out the peak frequency with maximum power. Then the third step makes sure that the power of the peak frequency is dominant over the power of other frequencies.

Figure 3:
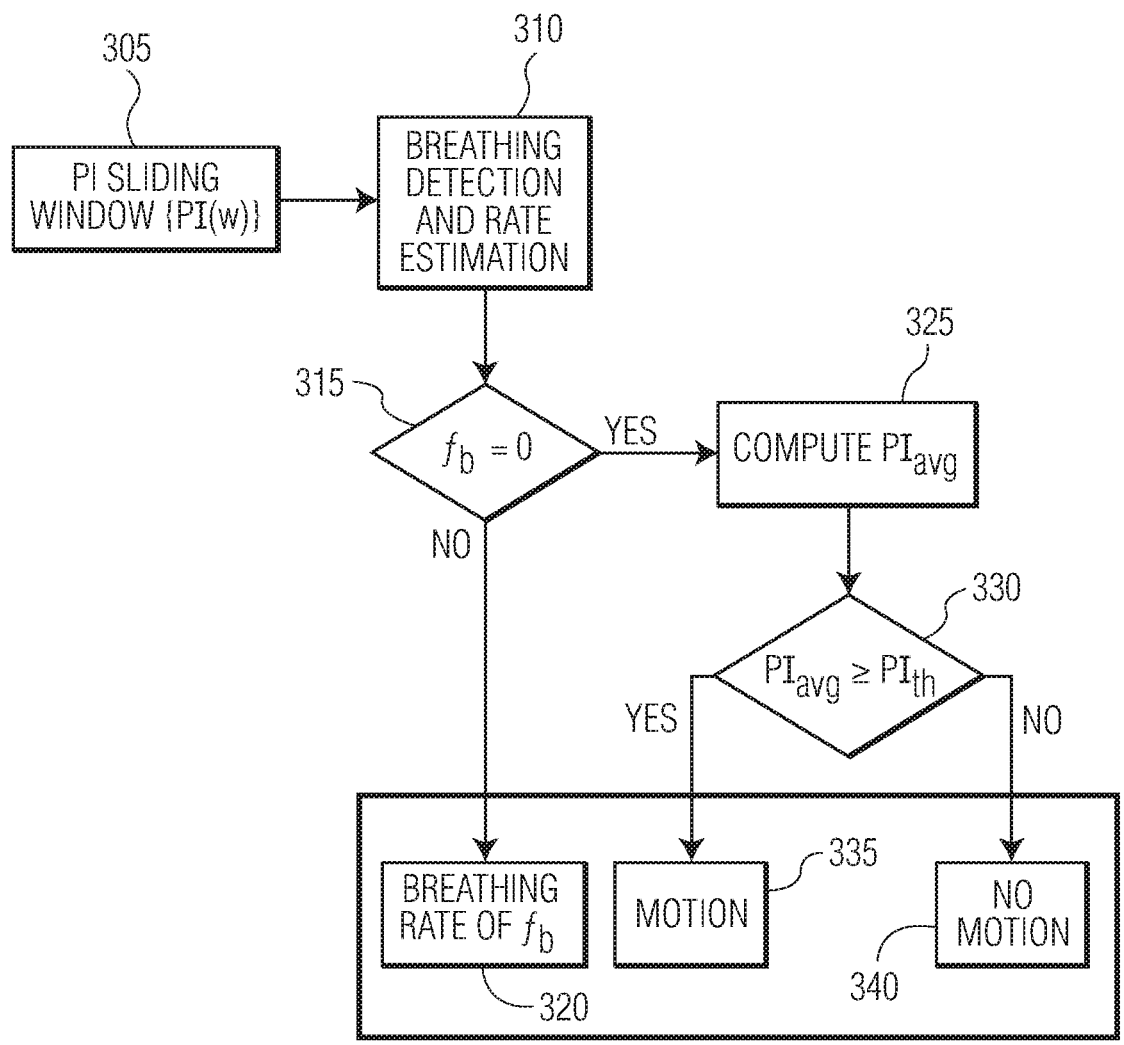
FIG. 3 illustrates a flow diagram showing how the system may be extended to detect human motion.

FIG. 3 illustrates a flow diagram showing how the system may be extended to detect human motion. The human status detection system is able to detect three statuses including breathing, motion, and no motion. For the breathing status, the individual stays still and only breathing causes wireless channel to change, e.g., while sleeping. For the motion status, the individual exhibits noticeable movement, e.g., tossing and turning or a baby crying. For the no motion status, no significant wireless environmental change is detected, e.g., an empty room or car.

The system determines the PI sliding window 305 and performs breathing detection and rate estimation 310 as described above. Next, it is determined if the breathing rate $f_b$ is zero 315. If not, then the breathing rate $f_b$ is output 320. If so, the system may the determine if there is human motion by computing the average of the PI values $PI_{avg}$. $PI_{avg}$ is then compared to a predetermined threshold $PI_{th}$ 330. If $PI_{avg}$ is greater than or equal to $PI_{th}$, then motion is indicated 335. If $PI_{avg}$ is less than $PI_{th}$, then motion is not indicated 340.

The wireless breathing detection and rate estimation system described herein is passive as the individual does not have to carry or touch any devices. As Wi-Fi devices are widely available, the breathing rate detection system may be built on top of wireless communication between devices and will have low cost and be almost installation free. The system may be readily applied to current Wi-Fi chips. The system provides a technological solution to the problem of detecting breathing and estimating breathing rate in a non-invasive manner and with a minimum installation using widely available wireless networks.

The breathing detection and rate estimation system described herein may be used in various scenarios. For example, when baby or child is left in a room, the system may send an alarm to the parent's cellphone to let them know someone is sleeping or moving in room. In another example, sleep quality may be measured by determining the breathing rate and then the length of sleep/non sleep time.

Figure 4:
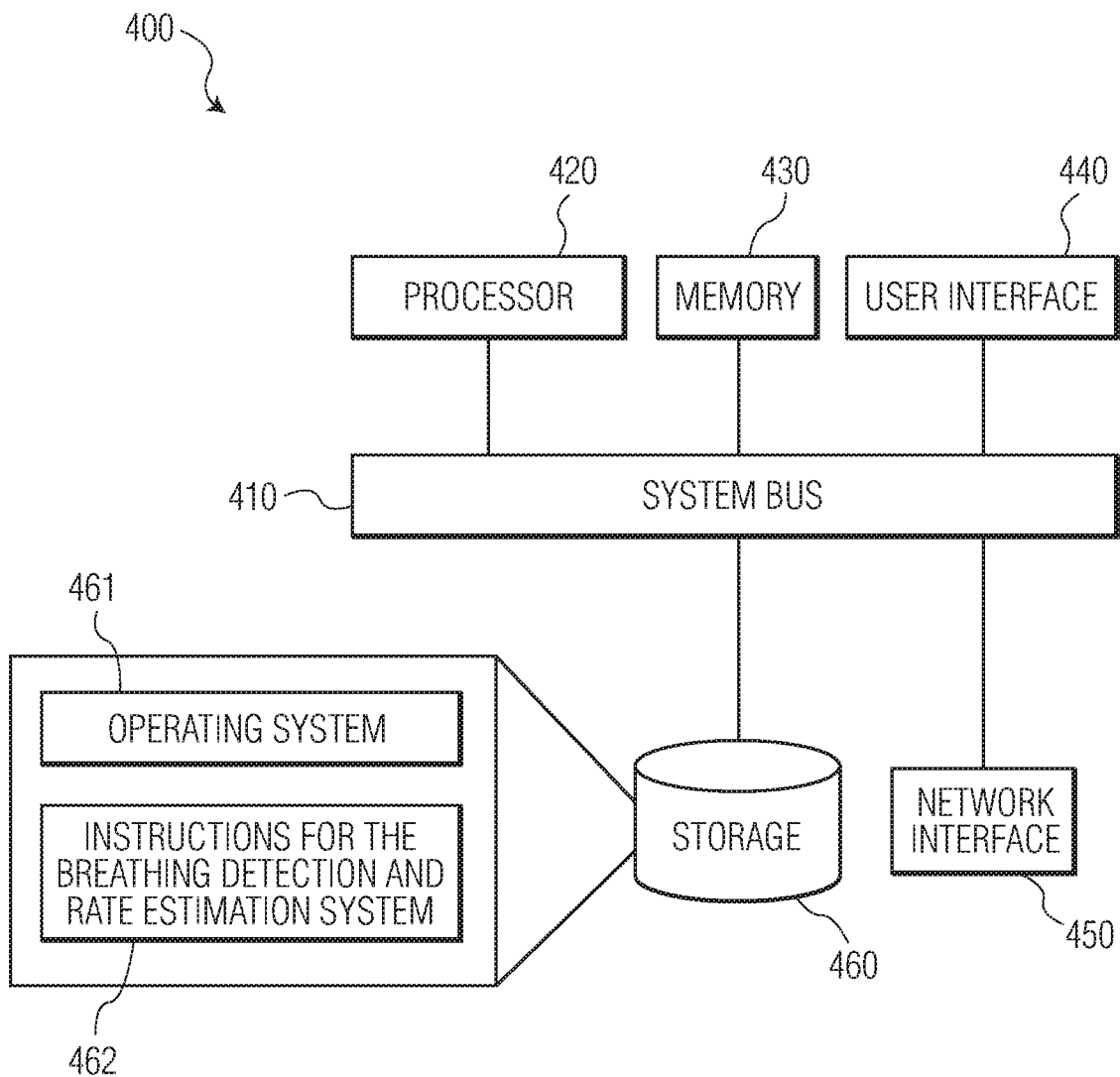
FIG. 4 illustrates an exemplary hardware device for implementing the breathing detection and rate estimation system.

FIG. 4 illustrates an exemplary hardware device 400 for implementing the breathing detection and rate estimation system. For example device 400 may be a Wi-Fi access point or other wireless access point, a client device like a mobile phone, a computer, etc. As shown, the device 400 includes a processor 420, memory 430, user interface 440, network interface 450, and storage 460 interconnected via one or more system buses 410. It will be understood that FIG. 4 constitutes, in some respects, an abstraction and that the actual organization of the components of the device 400 may be more complex than illustrated.

The processor 420 may be any hardware device capable of executing instructions stored in memory 430 or storage 460 or otherwise processing data. As such, the processor may include a microprocessor, a graphics processing unit (GPU), field programmable gate array (FPGA), application-specific integrated circuit (ASIC), any processor capable of parallel computing, or other similar devices. The processor may also be a special processor that implements machine learning models.

The memory 430 may include various memories such as, for example L1, L2, or L3 cache or system memory. As such, the memory 430 may include static random-access memory (SRAM), dynamic RAM (DRAM), flash memory, read only memory (ROM), or other similar memory devices.

The user interface 440 may include one or more devices for enabling communication with a user and may present information to users. For example, the user interface 440 may include a display, a touch interface, a mouse, and/or a keyboard for receiving user commands. In some embodiments, the user interface 440 may include a command line interface or graphical user interface that may be presented to a remote terminal via the network interface 450.

The network interface 450 may include one or more devices for enabling communication with other hardware devices. The network interface 450 may include a network interface card (NIC) configured to communicate according to the Ethernet protocol or other communications protocols, including wireless protocols. For example, the network interface 450 may be a Wi-Fi or other wireless interface whose signal is used to detect breathing. Such a wireless interface may include a transmitter/receiver and an antenna. Additionally, the network interface 450 may implement a TCP/IP stack for communication according to the TCP/IP protocols. Various alternative or additional hardware or configurations for the network interface 450 will be apparent.

The storage 460 may include one or more machine-readable storage media such as read-only memory (ROM), random-access memory (RAM), magnetic disk storage media, optical storage media, flash-memory devices, or similar storage media. In various embodiments, the storage 460 may store instructions for execution by the processor 420 or data upon which the processor 420 may operate. For example, the storage 460 may store a base operating system 461 for controlling various basic operations of the hardware 400. The storage 462 may store instructions for implementing the breathing detection and rate estimation system described herein.

It will be apparent that various information described as stored in the storage 460 may be additionally or alternatively stored in the memory 430. In this respect, the memory 430 may also be considered to constitute a "storage device" and the storage 460 may be considered a "memory." Various other arrangements will be apparent. Further, the memory 430 and storage 460 may both be considered to be "non-transitory machine-readable media." As used herein, the term "non-transitory" will be understood to exclude transitory signals but to include all forms of storage, including both volatile and non-volatile memories.

While the system 400 is shown as including one of each described component, the various components may be duplicated in various embodiments. For example, the processor 420 may include multiple microprocessors that are configured to independently execute the methods described herein or are configured to perform steps or subroutines of the methods described herein such that the multiple processors cooperate to achieve the functionality described herein. Such plurality of processors may be of the same or different types. Further, when the device 400 is implemented in a cloud computing system, the various hardware components may belong to separate physical systems. For example, the processor 420 may include a first processor in a first server and a second processor in a second server.

Any combination of specific software running on a processor to implement the embodiments of the invention, constitute a specific dedicated machine.

It should be appreciated by those skilled in the art that any block diagrams herein represent conceptual views of illustrative circuitry embodying the principles of the invention.

Although the various exemplary embodiments have been described in detail with particular reference to certain exemplary aspects thereof, it should be understood that the invention is capable of other embodiments and its details are capable of modifications in various obvious respects. As is readily apparent to those skilled in the art, variations and modifications can be affected while remaining within the spirit and scope of the invention. Accordingly, the foregoing disclosure, description, and figures are for illustrative purposes only and do not in any way limit the invention, which is defined only by the claims.

What is claimed is:

1. A method for estimating a breathing rate, comprising:
    receiving at a first wireless communication device a wireless signal from a second wireless communication device;
    measuring, by the first wireless communication device, a plurality of channel state information (CSI) data points from the wireless signal, wherein breathing-related motion over time changes the CSI data points between the first and second communication devices;
    selecting, by the first wireless communication device, an initial reference CSI data point from the plurality of CSI data points;
    computing, by the first wireless communication device, a first perturbation index curve for the wireless signal using the initial reference CSI data point and a portion of the plurality of CSI data points;
    finding, by the first wireless communication device, an optimal reference CSI data point from within the plurality of CSI data points associated with a maximum perturbance index value from within the first perturbation index curve;
    computing, by the first wireless communication device, a second perturbation index curve for the wireless signal using the optimal reference CSI data point and a portion of the plurality of CSI data points subsequent to the optimal reference CSI; and
    determining, by the first wireless communication device, the breathing rate from the second perturbation index curve using a frequency analysis.

2. The method of claim 1, wherein computing either the first or second perturbation index curves includes using channel nulling.

3. The method of claim 2, wherein channel nulling includes:
    calculating a nulling matrix; and
    applying the nulling matrix to the plurality of CSI data points.

4. The method of claim 1, wherein computing either the first or second perturbation index curves $\Gamma_n$ includes computing:

$$\Gamma_n = 10 \log_{10} |\Sigma_{k,k+1 \in \Psi} \overline{\Delta h}_k^n {}^H \overline{\Delta h}_{k+1}^n| - 10 \log_{10} \Sigma_{k,k+1 \in \Psi} \|h_k^n\|^2,$$

where $\overline{\Delta h}_k^n$ is channel change information for $CSI_n$, $h_k^n$ is the CSI for sample n, $\Psi$ is the set of all the available tones, and k is tone index.

5. The method of claim 1, wherein the frequency analysis of the second perturbation index curve includes applying a fast Fourier transform (FFT).

6. The method of claim 1, wherein determining the breathing rate includes:
    calculating a standard deviation of the second perturbation index curve over a window set of CSI data points; and
    indicating a breathing detection failure when the standard deviation is below a predetermined threshold value.

7. The method of claim 1, wherein the frequency analysis includes:
    performing a frequency transformation of the second perturbation index curve over a window set of CSI data points; and
    determining the breathing rate as a frequency with a highest value.

8. The method of claim 7, further comprising:
    calculating a peak-to-total power ratio using the frequency with the highest value; and
    indicating a breathing detection failure when the peak-to-total power ratio is below a predetermined threshold value.

9. The method of claim 7, further comprising sliding the window set of CSI data points and re-calculating the breathing rate.

10. The method of claim 7, further comprising:
    determining a breathing rate detection failure;
    computing an average of the second perturbation index curve values corresponding to the window set of CSI data points;
    indicating motion when the average of the second perturbation index curve values corresponding to the window set of CSI data points is above a predetermined threshold; and
    indicating no motion when the average of the second perturbation index curve values corresponding to the window set of CSI data points is below a predetermined threshold.

11. A breathing rate estimation device, comprising:
    a first wireless communication device configured to:
    receive a wireless signal from a second wireless communication device;
    measure a plurality of channel state information (CSI) data points from the wireless signal, wherein breathing-related motion over time changes the CSI data points between the first and second communication devices;
    select an initial reference CSI data point from the plurality of CSI data points;
    compute a first perturbation index curve for the wireless signal using the initial reference CSI data point and a portion of the plurality of CSI data points;
    find an optimal reference CSI data point from within the plurality of CSI data points associated with a maximum perturbance index value from within the first perturbation index curve;
    compute a second perturbation index curve for the wireless signal using the optimal reference CSI data point and a portion of the plurality of CSI data points subsequent to the optimal reference CSI; and
    determine the breathing rate from the second perturbation index curve using a frequency analysis.

12. The system of claim 11, wherein computing either the first or second perturbation index curves includes using channel nulling.

13. The system of claim 12, wherein channel nulling includes:
    calculating a nulling matrix; and
    applying the nulling matrix to the plurality of CSI data points.

14. The system of claim 11, wherein computing either the first or second perturbation index curves $\Gamma_n$ includes computing:

$$\Gamma_n = 10 \log_{10} |\Sigma_{k,k+1 \in \Psi} \overline{\Delta h}_k^{n \ H} \overline{\Delta h}_{k+1}^n| - 10 \log_{10} \Sigma_{k,k+1 \in \Psi} \|h_k^n\|^2,$$

where $\overline{\Delta h}_k^n$ is channel change information for $CSI_n$, $h_k^n$ is the CSI for sample n, $\Psi$ is the set of all the available tones, and k is tone index.

15. The system of claim 11, wherein the frequency analysis of the second perturbation index curve includes applying a fast Fourier transform (FFT).

16. The system of claim 11, wherein determining the breathing rate includes:
    calculating a standard deviation of the second perturbation index curve over a window set of CSI data points; and
    indicating a breathing detection failure when the standard deviation is below a predetermined threshold value.

17. The system of claim 11, wherein the frequency analysis includes:
    performing a frequency transformation of the second perturbation index curve over a window set of CSI data points; and
    determining the breathing rate as a frequency with a highest value.

18. The system of claim 17, wherein the first wireless communication device is further configured to:
    calculate a peak-to-total power ratio using the frequency with the highest value; and
    indicate a breathing detection failure when the peak-to-total power ratio is below a predetermined threshold value.

19. The system of claim 16, wherein the first wireless communication device is further configured to slide the window set of CSI data points and re-calculate the breathing rate.

20. The system of claim 16, wherein the first wireless communication device is further configured to:
    determine a breathing rate detection failure;
    compute an average of the second perturbation index curve values corresponding to the window set of CSI data points;
    indicate motion when the average of the second perturbation index curve values corresponding to the window set of CSI data points is above a predetermined threshold; and
    indicate no motion when the average of the second perturbation index curve values corresponding to the window set of CSI data points is below a predetermined threshold.

* * * * *